US006391590B1

(12) United States Patent
Sano et al.

(10) Patent No.: US 6,391,590 B1
(45) Date of Patent: May 21, 2002

(54) RECOMBINANT STREPTAVIDIN-METALLOTHIONEIN CHIMERIC PROTEIN HAVING BIOLOGICAL RECOGNITION SPECIFICITY

(75) Inventors: Takeshi Sano, Albany; Alexander N. Glazer, Orinda; Charles R. Cantor, Berkeley, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 07/780,717

(22) Filed: Oct. 21, 1991

(51) Int. Cl.$^7$ .................. C12N 15/62; C12N 15/63; C07K 14/36
(52) U.S. Cl. ............. 435/69.7; 435/69.1; 435/252.33; 435/320.1; 530/402; 530/350; 530/404; 530/413; 536/24.1
(58) Field of Search ................. 530/345, 402, 530/350, 413, 404; 435/69.7, 252.33, 320.1, 172.3, 69.1; 536/24.1

(56) References Cited

U.S. PATENT DOCUMENTS

| | | | | |
|---|---|---|---|---|
| 4,732,864 A | * | 3/1988 | Tolman | 530/402 |
| 4,772,691 A | * | 9/1988 | Herman | 536/27 |
| 4,839,293 A | | 6/1989 | Cantor et al. | 435/320 |
| 5,196,510 A | * | 3/1993 | Rodwell et al. | 530/326 |

FOREIGN PATENT DOCUMENTS

| | | | |
|---|---|---|---|
| WO | WO8602077 | | 4/1986 |
| WO | WO8809344 | | 12/1988 |
| WO | WO8909393 | | 10/1989 |
| WO | 9006323 | * | 6/1990 |

OTHER PUBLICATIONS

Weber et al. Structural origins of high–affinity biotin binding to streptavidin. Science, (Jan. 6, 1989) 243 (4887) 85–8.*
Hiller et al. Studies on the biotin–binding site of avidin. Minimized fragments that bind biotin. Biochem. J., (Sep. 1, 1991) 278 (Pt 2) 573–85.*
Kurzban et al. The quaternary structure of streptavidin in urea J. Biol. Chem. (Aug., 1991), 266(22), 14470–7.*
Hendrickson et al. Proc. Natl. Acad. Sci. vol. 86, pp. 2190–2194, Apr. 1989.*
Rudolph, R. "Renaturation of recombinant, disulfide–bonded proteins from inclusion bodies," In, Modern Methods of Protein and Nucleic Acid Research, 1990, pp. 149–171.*
Lowenadler et al "A gene fusion system . . . " *Gene 58*: 87–97 (1987).*
Rhodes et al "A Yeast–*Escherichia coli* Shuttle Vector . . . " *Plasmid 23*: 159–162 (Mar. 1990).*
Arnold et al "A family of high–copy–number plasmid vectors . . . " Gene 70: 171–179 (1988).*
Romeyer et al., "Bioaccumulation of heavy metals in *Escherichia coli* . . . ", *J. Biotech. 8*: 207–220, 1988.*
Butt et al., "Ubiquitin fusion augments the yield of cloned gene products . . . ", *PNAS 86*: 2540–2544, Apr. 1989.*
Argarana, C.E.; Kuntz, I.D.; Birken, S.; Axel, R.; Cantor, C.R. Molecular Cloning and Nucleotide Sequence of the Streptavidin Gene, *Nuc. Acids Res.*, 14:1871 (1986).
Sano, T., Cantor, C.R. Expression of a Cloned Streptavidin Gene in *Escherichia coli, Proc. Nat. Acad. Sci.*, 87:142–146 (1990).
Sano, T., Cantor, C.R. Expression Vectors for Streptavidin–containing Chimeric Proteins, *Bioch. Biophys. Res. Comm.*, 176:571–577 (1991).
Hamer, D.H., Metallothionein, *Ann. Rev. Biochem.*, 55:913–51 (1986).
Sano, T., Cantor, C.R., Cooperative Biotin Binding by Streptavidin, *J. Biol. Chem.*, 265: 3369–3373 (1990).
Bayer, E.A., Ben–Hur H., Wichek, M., Isolation and Properties of Streptavidin, *Meth. Enzym.*, 184: 80–89 (1990).
Green, M.N., Avidin and Streptavidin, *Meth. Enzym.*, 184: 51–67 (1990).
Kagi, J.H.R.; Schaffer, A. Biochemistry of Metallothionein, *Biochemistry*, 27:8509–8515 (1988).

* cited by examiner

*Primary Examiner*—David S. Romeo
(74) *Attorney, Agent, or Firm*—Richard Aron Osman (57) ABSTRACT

Streptavidin-metallothionein chimeric proteins with biological recognition specificity in which the streptavidin moiety provides high affinity biotin binding and the metallothionein moiety provides a high affinity metal binding. The binding affinity of the streptavidin-metallothionein chimeric protein both for biotin and heavy metal ions allows specific incorporation into, conjugation with, or labelling of any biological material containing biotin with various heavy metal ions.

27 Claims, 2 Drawing Sheets

RECOMBINANT STREPTAVIDIN-METALLOTHIONEIN CHIMERIC PROTEIN HAVING BIOLOGICAL RECOGNITION SPECIFICITY

This invention was made with Government support under Grant Contract No. CA39782 awarded by the National Cancer Institute, National Institutes of Health. The Government has certain rights in this invention.

BACKGROUND OF THE INVENTION

Field of Invention

This invention concerns streptavidin-metallothionein chimeric proteins which possess biological recognition specificity.

RELATED DISCLOSURES

Recombinant streptavidin-metallothionein chimeric proteins containing various metal ions are molecules which have a great potential in preventive and therapeutic medicine in both humans and animals as well as for diagnostic use. While each individual molecule, i.e., streptavidin and metallothionein have been known and described previously, their composite molecule has never before been constructed.

Biochemistry of metallothionein, particularly its amino acid sequence in various species, its metal binding sites, metal thiolate clusters and spatial structures are described in Biochemistry, 27:509 (1988). Ann. Rev. Biochem., 55:913 (1986) is directed to the gene structure, organization, amplification and transcriptional regulations, and describes also some genetic engineering applications, such as for example, metallothionein-rat growth hormone and metallothionein-human growth hormone genes expressed in transgenic mice, or conferring resistance to copper toxicity via the CUP 1 copper-metallothionein gene.

Streptavidin is a protein very closely related to a protein avidin which provides a very stable noncovalent complex with vitamin D-biotin. Avidin itself is a very highly specialized protein that is only rarely expressed. Streptavidin, on the other hand, is readily expressed in Streptomyces species particularly in Streptomyces avidinii. Streptavidin specifically binds a water soluble vitamin D-biotin (vitamin H). Similarly to avidin, it binds rapidly and almost irreversibly to any molecule which contains unhindered biotin with a remarkably high affinity. Streptavidin, contrary to avidin, is carbohydrate free and thus more suitable, for example, for X-ray crystallographic studies or for various other detection techniques. The comparative properties of avidins and streptavidins are described in Methods in Enzymology, 184:51 (1990). Isolation and properties of streptavidin, as well as its preparation, are described in Ibid., at page 80.

Expression of a cloned streptavidin gene in Escherichia coli is described in Proc. Natl. Acad. Sci., 87:142 (1990) and the cooperativity in the biotin binding to streptavidin is described in J. Biol. Chem., 265:3369 (1990).

SUMMARY

One aspect of the current invention is a recombinant streptavidin-metallothionein chimeric protein having biological recognition specificity.

Another aspect of the current invention is an expression system for the cloned streptavidin gene which expresses streptavidin in Escherichia coli and allows the expression of a streptavidin-metallothionein chimeric protein.

Another aspect of the current invention is an expression vector pTSAMT-2 constructed by inserting the mouse metallothionein-I cDNA into an expression vector for streptavidin-containing chimeric proteins pTSA-I8F.

Another aspect of the current invention is the expression of the gene fusion of streptavidin with metallothionein using T7 expression system.

Still another aspect of the current invention is the method for binding streptavidin-metallothionein chimeric protein with various metal ions.

Still yet another aspect of the current invention is incorporation of the metal-containing streptavidin-metallothionein chimeric protein into biological materials containing unhindered biotin.

Yet another aspect of the current invention is the method for introducing heavy metal ions into the tissue, removing the heavy metal ions from the tissue or labeling the tissue with heavy metal ions.

Still another aspect of the current invention is the use of the streptavidin-metallothionein chimeric protein for imaging of tumors, for radiotherapeutics, for labeling of biological materials, for detection of biological molecules present at very low levels and for simultaneous multi-mass labeling of short DNA molecules allowing determination of a number of DNA sequences.

DETAILED DESCRIPTION OF THE INVENTION

This invention concerns streptavidin-metallothionein chimeric proteins and their derivatives with biological recognition specificity. Specifically, it provides a recombinant streptavidin-metallothionein chimeric protein which can be efficiently expressed in Escherichia coli and purified by simple procedures. The purified chimeric protein can bind one biotin molecule and seven $Cd^{2+}$ ions per subunit. With the specific and tight binding affinity of the streptavidin-metallothionein chimeric protein both for the heavy metal ions and biotin, any biological material containing unhindered biotin may be conjugated and/or labeled with the heavy metal ions binding to metallothionein, and/or the heavy metal ions may be incorporated into any biological material which contains biotin, and/or heavy metal ion may be removed from the biological material.

The biological recognition specificity of the streptavidin-metallothionein chimeric protein of the current invention is conferred on that protein by streptavidin which specifically binds biotin with extremely high affinity and by metallothionein which binds various heavy metal ions with extremely high affinity. Since biotin can be easily incorporated into various biological substances, the streptavidin-biotin system offers an avenue by which the second system, namely metallothionein-bound heavy metal, such as Cd, Zn, Cu, Hg, Co, Fe, Pb, Ni, Bi, Sn, Au and Ag and their stable isotopes, as seen in Table 1, as well as their radioisotopes, can be incorporated into, conjugated with or used for labeling of biological materials.

TABLE 1

List of Heavy Metal Stable Isotopes That Can Be Bound by Metallothionein

| | | | |
|---|---|---|---|
| $_{26}$Fe | $^{54}$Fe | $_{50}$Sn | $^{112}$Sn |
| | $^{56}$Fe | | $^{114}$Sn |
| | $^{57}$Fe | | $^{115}$Sn |
| | $^{58}$Fe | | $^{116}$Sn |
| $_{27}$Co | $^{59}$Co | | $^{117}$Sn |
| $_{28}$Ni | $^{59}$Ni | | $^{118}$Sn |
| | $^{60}$Ni | | $^{119}$Sn |
| | $^{61}$Ni | | $^{120}$Sn |
| | $^{62}$Ni | | $^{122}$Sn |
| | $^{64}$Ni | | $^{124}$Sn |
| $_{29}$Cu | $^{63}$Cu | $_{79}$Au | $^{197}$Au |
| | $^{65}$Cu | $_{80}$Hg | $^{196}$Hg |
| $_{30}$Zn | $^{64}$Zn | | $^{198}$Hg |
| | $^{66}$Zn | | $^{199}$Hg |
| | $^{67}$Zn | | $^{200}$Hg |
| | $^{68}$Zn | | $^{201}$Hg |
| | $^{70}$Zn | | $^{202}$Hg |
| $_{47}$Ag | $^{107}$Ag | | $^{204}$Hg |
| | $^{109}$Ag | $_{82}$Pb | $^{204}$Pb |
| $_{48}$Cd | $^{106}$Cd | | $^{206}$Pb |
| | $^{108}$Cd | | $^{207}$Pb |
| | $^{110}$Cd | | $^{208}$Pb |
| | $^{111}$Cd | $_{83}$Bi | $^{209}$Bi |
| | $^{112}$Cd | | |
| | $^{113}$Cd | | |
| | $^{114}$Cd | | |
| | $^{116}$Cd | TOTAL | 50 Species |

Mammalian metallothioneins are 61- or 62-residue polypeptides containing 20 cysteine residues. The amino terminal methionine residue is acetylated.

The consensus amino acid sequence of mammalian metallothioneins is:

```
              1                              29
    β  N-Ac-MDPNCSCATGGSCTCAGSCKCKECKCTSC 30                         61
    α  KKSCCSCCPVGCAKCAQGCVCKGASDKCSCCA     SEQ ID NO:5
```

The 61-residue molecule folds into two domains, α and β, each of which contains a metal cluster. The crystal structure of rat cadmium, zinc-metallothionein II shows that the folding of the metal-binding portion of the β domain is independent of the amino-terminal two residues. There are 20 invariant cysteinyl residues in mammalian metallothioneins (indicated as C in the sequence). There are relatively few contacts between the α and β domains and the separated α and β domains bind metals with the same stoichiometry as in the intact molecule.

Metal ions are bound to metallothioneins exclusively through the cysteinyl residues. The metals can be removed from metallothionein by exposure to acid pH and the resulting apoprotein can be reconstituted with seven $Cd^{++}$ ions, or seven $Zn^{++}$ ions, or twelve $Cu^+$ ions. Similarly, mammalian metallothionein can bind seven atoms of Hg, Co, Fe, Pb, Ni, Bi, Sn, or up to twelve atoms of silver and gold. Stability constants range from $10^{19}$ to $10^{17}$ for Cu, $10^{17}$ to $10^{15}$ for Cd, and $10^{14}$ to $10^{11}$ for Zn. The crystal structure determination shows that each metal ion is tetrahedrally coordinated to four cysteinyl sulfurs.

Streptavidin

Streptavidin is a protein closely related to avidin. Like avidin, streptavidin was found to bind rapidly and almost irreversibly to any molecule containing unhindered biotin with specific affinity Kd≈$10^{-15}$M. *J. Biol. Chem.*, 265:3369 (1990) describes the cooperative biotin binding by streptavidin. Streptavidin contains no carbohydrate and has a slightly acid isoelectric point which minimizes nonspecific absorption to nucleic acids and negatively charged cell membranes.

Streptavidin can be isolated from culture broth of *Streptococcus avidinii* according to methods described in *Arch. Biochem. Biophys.*, 106:1 (1964) and in *Methods in Enzymology*, 184:51 and 80 (1990). Streptavidin has an apparent molecular weight of about 66,000 and is capable of binding one mole of biotin per mole of subunit. The thermal stability of streptavidin is remarkable. In the presence of SDS, streptavidin begins to dissociate to its monomers and dimers only at temperatures above 60° C.

Expression of Streptavidin and Metallothionein

Cloning and sequencing of the streptavidin gene was described in *Nucleic Acid Res.*, 14:1871 (1986). Streptavidin has a sequence of 159 amino acids, some 30 residues longer than avidin.

Most commercial preparations contain "core" streptavidin of 125–127 residues. This core has a much higher solubility in water than its unprocessed precursor and is identical to avidin at 33% of its residues, including the four tryptophan residues involved in the biotin-binding site. The streptavidin gene is extremely lethal to the host cells, because of the strong biotin binding of the gene products.

Consequently, the expression of a cloned streptavidin gene in *Escherichia coli* using T7 expression systems, described previously by inventors in *Proc. Natl. Acad. Sci.*, 87:142 (1990), is of the utmost importance for practice of this invention. Using particularly the procedure described *Ibid.*, at page 142 and 143, streptavidin purified almost to homogeneity was obtained. Streptavidin purified by this procedure is able to bind 3.5–3.9 molecules of biotin per molecules, having thus almost the full binding capacity of the non-recombinant molecule (natural product).

Metallothionein genes are inducible, selectible and expressed at high levels. The metallothionein genes all share a similar structure in which two introns interrupt three exons at precisely homologous positions. Isolation of complementary cDNA clones has been reported for mouse MT-I and MT-II, human MT-I and MT-II, monkey MT-I and MT-II, chinese hamster MT-I and MT-II, rat MT-I; sheep MT-I, and chicken MT.

The gene for *Neurospora crassa* copper-metallothionein has been recently synthesized and its expression in *E. coli* was described in *J. Biochem.*, 104:924–926 (1988), where the synthesis of the gene encoding the *N. crassa* copper-metallothionein gene was achieved with amino acid codons most commonly used in *E. coli*, flanked by initiation (ATG) and termination codons (TAA). When this gene was ligated into an expression vector, however, very low yields of metallothionein were obtained and only in the early stage of the cultivation of the *E. coli* cells. It was therefore concluded that the metallothionein obtained in this way was being somehow degraded. The synthetic metallothionein gene was then fused in frame to the amino-terminal portion of μ-galactosidase with α-complementation activity. Immunoaffinity chromatography on an anti-β-galactosidase antibody column gave a reasonable yield (10% of soluble protein) of the fusion protein.

Metallothionein gene expression is rapidly and transiently induced by exposure to heavy metals and, in mammalian cells, by exposure to various circulating factors such as hormones and interferon.

Metallothionein used in the chimeric protein of the current invention may be expressed in any suitable way previously described or, preferably, by using the pTSAMT-2 vector of this invention.

Expression Vectors for Streptavidin-Containing Chimeric Proteins

Figure 1:
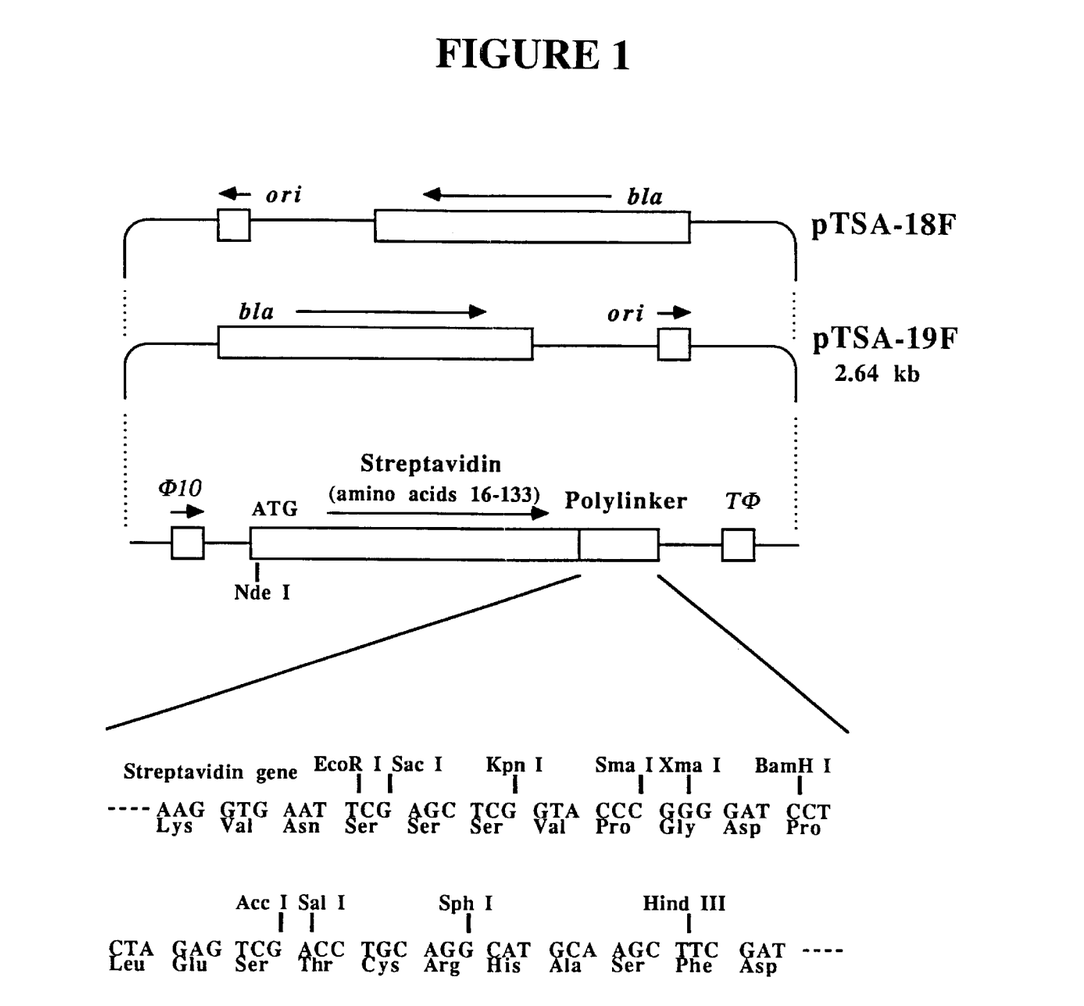
FIG. 1 represents expression vectors pTSA-18F and pTSA-19F for streptavidin-containing chimeric proteins. The polylinker cDNA (SEQ ID NO:1) and amino acid (SEQ ID NO:2) sequences are shown.

Recently, gene expression systems have been developed to characterize functional genes and their encoded proteins. The genes of interest were fused to another gene encoding a marker protein and expressed as chimeric proteins, which facilitated purification and characterization of the expressed protein. Utilizing the strong binding properties of the streptavidin-biotin complex, the newly developed expression system for streptavidin, as described above, allows the use of streptavidin as a powerful marker protein via streptavidin-containing chimeric proteins. For this purpose, expression vectors pTSA-18F and pTSA-19F described in *Biochem. Biophys. Res. Commun.*, 176:571 (1991), shown in FIG. 1, were constructed. Unique cloning sites are indicated. These vectors carry most of the streptavidin gene, which encodes amino acid residues 16 to 133 (SEQ ID NO:7. cDNA coding sequence is SEQ ID NO:6) of the mature streptavidin. The DNA sequences corresponding to both these molecular termini have been truncated, because the termini cause aggregation of the molecules and are susceptible to proteolysis. The truncated streptavidin gene is flanked by a translation initiation codon and a polylinker derived from pUC19. Several unique cloning sites are found at the translation initiation site and in the polylinker. The coding region is then placed under control of the T7 promoter Φ10 and followed by the T7 transcription terminator TΦ, according to *Methods Enzymol.*, 185:60 (1990). These sequences were cloned into a fragment of pBR322 containing the replication origin and the bla gene. Methods and procedures used in the construction of these expression vectors are described in *Molecular Cloning: A Laboratory Manual*, Cold Spring Harbor Press (1989).

Gene fusions of streptavidin with a target protein are constructed by inserting a coding sequence of the target protein into one of the unique cloning sites. A chimeric protein of streptavidin and the target protein is expressed in *Escherichia coli* by using the T7 expression system, as reported in *Proc. Natl. Acad. Sci.*, 87:142 (1990) for a recombinant streptavidin. Because of the high toxicity of the gene products caused by the streptavidin moiety, the presence of a plasmid carrying the T7 lysozyme gene, such as pLysS and pLysE, is indispensable to maintain the vector stably in the host cells.

Streptavidin-containing chimeric proteins can be specifically detected and isolated by their biotin-binding.

Construction of Expression Vector for Streptavidin-Metallothionein Chimeric Protein The expression vector for the streptavidin-metallothionein chimeric protein was constructed by using a mouse metallothionein-I cDNA and an expression vector for streptavidin-containing chimeric proteins pTSA-18F. The mouse metallothionein-I cDNA was inserted into the pTSA-18F expression vector. The encoded chimeric protein has the metallothionein moiety following the core region of streptavidin with ten additional amino acids between the two moieties, as seen in FIG. 2.

Figure 2:
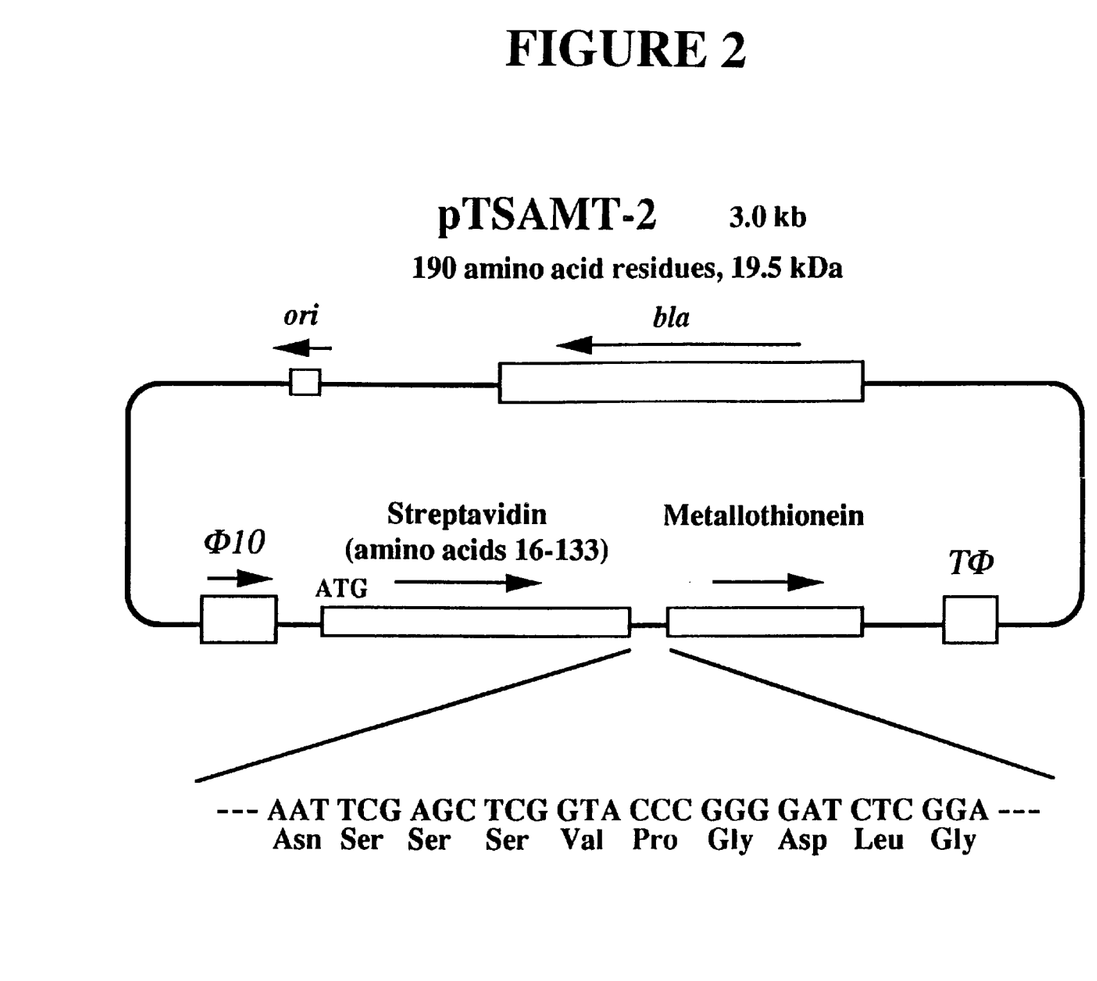
FIG. 2 represents the expression vector pTSAMT-2 for a streptavidin-metallothionein chimeric protein. The spacer cDNA (SEQ ID NO:3) and amino acid (SEQ ID NO:4) sequences are shown.

FIG. 2 represents expression vector pTSAMT-2 for a streptavidin-metallothionein chimeric protein. Construction of the expression vector was carried out by the standard methods described in *Molecular Cloning, A Laboratory Manual*, Cold Spring Harbor Press (1989). A 300 bp Bgl I-BamH I fragment of the mouse metallothionein-I cDNA described in *Nature*, 292:267 (1981) which carries the entire coding region was cloned into the BamH I site of pTSA-18F. The clone in which the metallothionein-I gene has the same orientation as the streptavidin gene was used as the expression vector, pTSAMT-2 (3.0 kb), shown in FIG. 2. The coding sequence is flanked by the Φ10 promoter and the TΦ transcription terminator. bla is β-lactamase gene; ori is replication origin.

pTSAMT-2 expression vector encodes a 19.5 kDa protein consisting of 190 amino acid residues, in which the metallothionein moiety follows the C-terminus of streptavidin. Ten additional amino acid residues, namely—Asn-Ser-Ser-Ser-Val-Pro-Gly-Asp-Leu-Gly—SEQ ID NO:4 which are derived from the polylinker region of pTSA-18F and the 5'-terminal region of the Bgl I-BamH I fragment of the mouse metallothionein-I cDNA, are present between two moieties. The amino acid composition of the encoded streptavidin-metallothionein chimeric protein obtained from the deduced amino acid sequence is shown in Table 2.

TABLE 2

Amino Acid Composition of Streptavidin-Metallothionein Chimeric Protein Encoded in pTSAMT-2

| Amino Acid | Number |
| --- | --- |
| Lys | 10 |
| His | 2 |
| Arg | 4 |
| Asp | 7 |
| Asn | 10 |
| Thr | 24 |
| Ser | 21 |
| Glu | 4 |
| Gln | 4 |
| Pro | 4 |
| Gly | 23 |
| Ala | 20 |
| Cys | 20 |
| Val | 10 |
| Met | 2 |
| Ile | 3 |
| Leu | 8 |
| Tyr | 6 |
| Phe | 2 |
| Trp | 6 |
| Total | 190 |
| Molecular Mass | 19.5kDa |

Table 2 shows that there are total of 190 amino acids present in the streptavidin-metallothionein chimeric protein encoded in pTSAMT-2. From the deduced amino acid sequence, the molecular mass of the chimeric protein was calculated to be 19.5 kDa.

Expression of Streptavidin-Metallothionein Chimeric Protein

Expression of the gene fusion of streptavidin with metallothionein was carried out by using the T7 expression system, described above, with which it was possible to successfully express a cloned streptavidin gene in *E. coli*. BL21 (DE3) (pLysE) was found to express the chimeric protein more efficiently than the equivalent lysogen carrying pLysS.

Lysogen BL21 (DE3) (pLysE) transformed with the expression vector pTSAMT-2 was grown at 37° C. with shaking in M9 minimal medium supplemented with 1 mM $MgSO_4$, 0.2% D-glucose, 1.5 µM thiamine (vitamin B1), 0.5% Casamino acids (Difco Laboratories), 2 µg/ml biotin, 150 µg/ml ampicillin, and 25 µg/ml chloramphenicol. While it is possible to use other suitable growth media, the minimal medium was found to reduce advantageously the proteolysis of the expressed chimeric protein substantially. When the absorbance at 600 nm of the culture reached values around 0.6, 100 mM of aqueous solution of isopropyl β-D-thiogalactopyranoside was added to a final concentration of 0.5 mM to induce the T7 RNA polymerase gene placed under lacUV5 promoter. After the induction, the cells were incubated at temperatures between 25–40° C., preferably at 37° C., with shaking for 3–7 hours, preferably 5 hours. In general, the streptavidin-metallothionein chimeric protein expressed by this technique reached more than 30% of the total cell protein approximately 5 hours after the induction.

Expression of streptavidin-metallothionein chimeric protein was studied by the SDS-PAGE containing the total cell protein during expression.

These findings show that there is a positive expression of streptavidin-metallothionein protein under these conditions in the samples which contained lysogen BL21 (DE3) (pLysE) with pTSAMT-2 starting already one hour after the induction. Such expression is dependent on time after the induction. With time, the 21 kDa band grows more intense, as seen following the Coomassie Brilliant Blue staining.

SDS-PAGE of the total cell protein during expression shows a major band at 21 kDa after the induction of the T7 RNA polymerase gene. However, the molecular mass of the major band at 21 kDa was higher than 19.5 kDa estimated from the deduced amino acid sequence as discussed above. To address the apparent discrepancy between theoretical 19.5 kDa molecular mass protein estimated and 21 kDa molecular mass protein obtained and to determine if the 21 kDa protein was the streptavidin-metallothionein chimeric protein, the proteins were pulse-labelled with [$^{35}$S] cysteine during expression. Because of the high cysteine content of the chimeric protein, 20 cysteine residues per subunit (190 residues) derived solely from the metallothionein moiety, the metallothionein moiety of the expressed chimeric protein should be strongly labeled with the radioactive cysteine. The proteins obtained when the lysogen BL21 (DE3) (pLSE) containing expression vector pTSAMT-2 was used for expression of the chimeric proteins were pulse-labelled with [$^{35}$S] cysteine during expression.

Autoradiography of the gel shows that the [$^{35}$S] cysteine is almost exclusively incorporated into the 21 kDa protein. This result reveals that the 21 kDa protein is cysteine-rich and thus is the streptavidin-metallothionein chimeric protein. The discrepancy in the molecular masses of the chimeric protein shown between the SDS-PAGE (21 kDa) and between the deduced amino acid sequence (19.5 kDa) is described below.

For cloning and expression, *E. coli* strains HMS174 (F$^-$ hsdR recA Rif$^R$) described in *Proc. Natl. Acad. Sci.*, 75:2276 (1978), BL21 (F$^-$ ompT hsdS gal) described in *J. Mol. Biol.*, 189:113 (1986) and *J. Bacteriol.*, 170:1245 (1988), DH5α described in *Molecular Cloning: A Laboratory Manual*, Cold Spring Harbor Press (1989) were used. BL21(DE3) is a lysogen with the λ derivative integrated into the chromosome. DE3 carries the T7 RNA polymerase gene under the lacUV5 promoter in the int gene. These strains were gifts from F. W. Studier (Brookhaven National Laboratory).

Purification and Characterization of Streptavidin-Metallothionein Chimeric Protein The expressed streptavidin-metallothionein chimeric protein was purified to homogeneity by a simple purification procedure including affinity chromatography using 2-iminobiotin as the ligand described in Example 2. After complete denaturation of the expressed chimera which formed inclusion bodies in the cells, renaturation in the presence of heavy metal ions such as $Cd^{2+}$ and $Zn^{2+}$ provided the chimera with additional stability, which allowed frozen storage and lyophilization. By this procedure, the yield of the purified chimera ranged from 0.8–1.2 mg per 100 ml culture.

The subunit dimer and tetramer are also observed on SDS-PAGE, though the protein sample was heated in boiling water for 5 minutes in the presence of 3% SDS and 10 mM DTT. Although natural streptavidin shows the subunit oligomers on SDS-PAGE, the amounts of such molecules for chimera seem greater than those for natural streptavidin. It is not clear, however, why the subunit association of the chimera in the presence of SDS is tighter than that of natural streptavidin. It is possible that intersubunit disulfide bonds, which are not completely cleavable even by DTT, are associated with the subunit oligomer formation. The purified streptavidin-metallothionein chimeric protein was subjected to SDS-PAGE. Approximately, 6 μg of the purified chimeric protein was applied to a 15% acrylamide gel. The polyacrylamide gel electrophoresis conditions were those described in *Nature*, 227:680 (1970). The right lane shows the positions of the molecular mass standard proteins of 94 kDa, 67 kDa, 43 kDa, 30 kDa, 20.1 kDa and 14.4 kDa.

The streptavidin-metallothionein chimera containing $^{109}Cd^{2+}$ described in Example 4 was also subjected to SDS-PAGE. Autoradiogram of the gel indicates that the chimera retains the bound heavy metal ions even after heating in boiling water for 5 minutes in the presence of 3% SDS and 10 mM DTT.

The result demonstrates the extreme stability of the chimera-heavy metal ion complexes. The higher apparent molecular mass of the chimera on SDS-PAGE is explainable by the bound heavy metal ions, which provide the chimera with additional positive charges resulting in slower migration on SDS-PAGE.

Biotin-binding ability was determined by gel filtration method, according to Methods Enzymol., 18A:424 (170), using a PD-10 column obtained from Pharmacia-LKB and D-[carbonyl-$^{14}$C] biotin of specific activity 53 mCi/mmol obtained from Amersham. Metal-binding ability was determined by quantitative X-ray fluorescence analysis as described in Example 3.

The purified streptavidin-metallothionein chimeric protein bound 0.99 molecules of biotin per subunit (19.5 kDa), indicating that the chimera had full biotin-binding ability. In addition, the purified chimera bound 6.7±1.0 molecules of $Cd^{2+}$ per subunit, determined by quantitative X-ray fluorescence analysis. Since mammalian metallothioneins bind a maximum of seven $Cd^{2+}$ per molecule, this result indicates that the metallothionein moiety of the chimera is also fully functional.

Gel filtration chromatography was carried out using a Sephacryl S-300 HR column (1.6×85 cm) at room temperature. The purified chimera (5.4 μg, 0.28 nmol subunits) was saturated with biotin by adding excess amounts of D-[carbonyl-$^{14}$C]biotin (53 mCi/mmol), and applied to the column previously equilibrated with TBS containing 0.05 % Tween 20. The proteins were eluted with the same solution at a flow rate of 24 ml/hr, and fractionated. The radioactivity of each fraction (2.66 ml) was determined by liquid scintillation counting (Tri-Carb 2000CA, Packard) with Ready Safe scintillation fluid (Beckman). The molecular mass was estimated by calibration with molecular mass standard proteins.

On gel filtration chromatography, the molecular mass of the chimera was estimated to be approximately 85 kDa, indicating that the chimera forms a subunit tetramer. This result also reveals that the subunit association of the chimera is determined by the streptavidin moiety. Therefore, one streptavidin-metallothionein chimeric protein consisting of four subunits binds four biotin molecules and 28 $Cd^{2+}$. Although aggregation of the chimera was sometimes observed when frozen-stored samples were used, the amounts of such aggregates were less than 15% of the total protein. However, such aggregate molecules also retained biotin-binding ability.

Conjugation and/or Labeling Biological Materials With Heavy Metal Ions Using Streptavidin-Metallothionein Chimeric Protein To demonstrate the capability of the streptavidin-metallothionein chimeric protein to specifically introduce heavy metal ions into biological macromolecules, the chimera containing $^{109}Cd^{2+}$ was targeted to biotinylated peroxidase immobilized on a nitrocellulose membrane. Various amounts of biotinylated peroxidase were immobilized on a nitrocellulose membrane, and the chimera containing $^{109}Cd^{2+}$, prepared by the method described in Example 4, was targeted to the immobilized biotinylated peroxidase. Autoradiography of the nitrocellulose membrane shows that the biotinylated peroxidase was specifically labeled with $^{109}Cd^{2+}$. This result clearly indicates that the bound heavy metal ions of the metallothionein moiety of the chimera were specifically attached to the biotinylated peroxidase by the chimera. The result also documents that the chimera is capable of binding both biotin and heavy metal ions simultaneously. Since extensive washing steps were included in this system, the results indicate that the chimera retains the tight binding affinity both for biotin and heavy metal ions that the natural streptavidin and metallothionein molecules possess. This is also supported by the fact that no background signal from non-specific binding of the chimera or the $^{109}Cd^{2+}$ to the blocker molecules (gelatin) was detectable.

In general, the chimeric protein can be saturated with heavy metal ions by mixing with a solution containing heavy metal ions of interest at neutral pH ranges as described in Examples 2 and 4. Because the metal-binding affinity of metallothionein is extremely high, excessive amounts of heavy metal ions are unnecessary, and free metal ions can be easily and almost completely removed by dialysis, filtration, or gel filtration chromatography. The chimeric protein saturated with heavy metal ions can be conjugated with any biological materials containing unhindered biotin by mixing them at any pH with except one of extreme acidity or alkalinity. Because both biotin and heavy metal binding affinity are remarkably high, no heavy metal ions, their stable isotopes, their radioisotopes, or biotinylated biological materials will be released from the conjugate under any conditions except for extremes of pH.

As seen from the results discussed above, using techniques as described herein, these chimeric protein may be advantageously manipulated to attach heavy metal ions or to release the metal ions from the chimeric protein molecule. By, for example, increasing the acidity, metal ions may be successfully and rapidly released from the chimeric protein. At neutral pH, however, the metal ions may be easily attached to the chimeric protein. The chimeric proteins labelled with heavy metal ions are fairly stable as long as the pH is maintained in a reasonable range. Only under extreme acidic or alkaline conditions, is the interaction disrupted.

The streptavidin-metallothionein chimeric protein of the current invention is designed at the DNA level. The chimeric or synthetic DNAs are expressed in any suitable host system preferably in *E. coli,* and the expressed proteins are collected, purified and/or renatured if necessary. A bifunctional protein is produced having a binding region whose metal binding specificity is determined by the metallothionein portion of the protein, and biotin binding specificity is determined by the streptavidin portion of the protein.

Utility of the complex, metal-containing chimeric proteins of the invention may depend on bioactive materials such as enzymes, toxins, growth factors, cell differentiation factors, receptors, anti-metabolites, hormones or various cytokines or lymphokines to which these metal containing chimeric protein may attach.

The two proteins making up the streptavidin-metallothionein domains may be further fused using all known conventional techniques, or assembled from synthesized oligonucleotides, and then expressed using equally conventional techniques. One method for obtaining DNA encoding the proteins disclosed herein is by assembly of synthetic oligonucleotides produced in a conventional, automated, polynucleotide synthesizer followed by ligation with appropriate ligases. All processes for manipulating, amplifying, and recombining DNA which encodes amino acid sequences of interest, or for identifying and isolating genes, their expression and their use in practice of this invention, are generally well known in the art. All are contemplated to be within the scope of the invention.

UTILITY

The streptavidin-metallothionein chimeric proteins of this invention are capable of being conjugated with or labeling biological materials with various heavy metal ions upon biotinylation. Their double specificity and high affinity binding to both biotin and heavy metal ions enables these proteins to be easily incorporated into various biological materials, including proteins, nucleic acids, carbohydrates, lipids, cells and tissues through the biotin binding sites. This ability expands the utility of these chimeric proteins to a broad range of biological materials.

The utility of these proteins include multiple labelling of various biological materials with different heavy metal ions, their stable isotopes, or their radioisotopes. Because the binding affinity of this chimeric protein both for biotin and heavy metal ions is extremely high, exchange reactions are prevented and the protein binds to any biological material containing unhindered biotin as a complex streptavidin-metallothionein-metal molecule. Because of the tightness of binding on both sides, i.e. streptavidin side to biotin and metallothionein to the heavy metal ions, under the normal reaction conditions, the exchange or dissociation of the molecule is prevented and the chimeric protein complex confers whatever heavy metal ion is bound to it to the biological material which is or may be biotinylated.

Streptavidin-metallothionein chimeric proteins of the current invention have unique properties. Their ability to react quickly and bind with a high specificity both heavy metal ions and biotin give them biological recognition specificity which is very useful for incorporating these proteins into biological materials, conjugating these proteins with biological materials or labeling the biological materials. In this way, these proteins may selectively confer, introduce, transfer or remove the heavy metal to or from the tissue, biological material or the bodily fluids.

No methods have been reported previously to provide metallothionein with biological recognition specificity. The novel metallothionein-streptavidin chimeric proteins of the current invention are able to specifically introduce heavy metal ions into biological molecules or remove these ions from such molecules.

Similarly, no chimeric proteins having the same or similar ability have been proposed for use in laboratories, research or industry.

One specific utility of the streptavidin-metallothionein chimeric protein of this invention is its usefulness for imaging of tumor cells and for radiotherapeutics.

Monoclonal antibody technology allows the specificity of an antibody molecule for its antigen (epitope) to be exploited in targeting antibodies or antibody conjugates to tumor cells. Agents for cancer radiotherapy and for diagnostic uses have been previously prepared by covalently attaching any of a variety of metal-chelating agents to antibodies, followed by conjugation of metal ions, usually a radionuclide, to the antibody containing the chelating agents. Many monoclonal antibodies show optimal tumor localization images only after a few days. Consequently, the choice of radionuclide with an appropriate half-life is essential. The gamma ($\gamma$)-emitting isotope $^{111}$In, for example, which has a 68 hour half-line and emits gamma-rays, with energies of 173 keV and 247 keV, is a radionuclide well-suited to tumor imaging. Copper-67 ($^{67}$Cu) is one of the most promising radiometals both for radioimmunotherapy and imaging, because of its 61.6 hour physical half-life, abundant beta particles, and gamma emissions. Paramagnetic complexes, such as those of Mn (III), Fe (III), and Gd (III), have also been used as contrast agents for magnetic resonance imaging. These approaches have been carried out with various metal ions. In all these instances, it is important that the chelating agent-metal ion complexes have a high kinetic inertness to avoid transfer of the metal ions to competing serum proteins such as transferrin and albumin. Monoclonal antibodies labeled with biotin have been very widely used in conjugates for cell sorting and cell analysis. In general, a modest degree of biotinylation, followed by complex formation with streptavidin, does not affect the immunoreactivity of the antibody.

The streptavidin-metallothionein chimeric protein of this invention, thus, can be loaded with any of a number of metal ions or radionuclides, particularly suitable for either imaging or radiotherapeutic uses, and attached to any desired biotinylated monoclonal antibodies. The binding constants of many metal ions to metallothionein are very high, and the complexes are extraordinarily kinetically inert. Consequently, antibodies conjugated to the metal loaded chimeric protein combine the advantages of high metal ion number per antibody molecule with high stability of the chelates. Procedure useful for such tumor imaging and radiotherapy is described in Example 6.

The use of avidin-metallothionein chimeric proteins may have some advantages for this application. An avidin-metallothionein chimeric protein can be produced by using a similar expression vector carrying the coding sequence for avidin, instead of the streptavidin gene, with the same methods used for the streptavidin-metallothionein chimeric protein as described above. Because avidin is produced by birds, reptiles and amphibia, while streptavidin is a bacterial protein, avidin-metallothionein chimeric proteins may have less antigenicity and thus have reduced immune responses in a body. This characteristics should allow administration of higher amounts of proteins containing radiometals into a body.

Metal-conjugated streptavidin-metallothionein can be easily separated and detected by gel filtration, reversed phase high pressure liquid chematography or gel electrophoresis. Similarly, the detection of these chimeric proteins may be achieved by using specific polyclonal and monoclonal antibodies in immunodiffusion, immunoelectrophoresis and radioimmuno-assays. The ease of their detection would be very useful for diagnostic purposes.

Another utility of this invention is labeling biological materials such as DNA and proteins, with heavy metal ions, their stable isotopes, or their radioisotopes using the streptavidin-metallothionein chimeric protein of this invention.

Recent development of biotinylation methods allows incorporation of biotin molecules to almost any kind of biological materials, including proteins, nucleic acids, carbohydrates, lipids, cells, and tissues. Such biotinylated materials can be easily conjugated to the streptavidin-metallothionein chimeric protein by simply mixing two components at an appropriate ratio. Since the metallothionein moiety of the chimeric protein is able to bind a variety of heavy metal ions, their stable isotopes, and their radioisotopes, conjugation of a biotinylated biological material to the chimeric protein containing one of such metal ions provides an easy and versatile way to specifically label the biological material. This allows detecting and tracking the biological material by various sensitive methods for heavy metals, including X-ray fluorometry, polarography, atomic absorption spectrometry, mass spectrometry, anodic stripping voltammetry, inductively coupled plasma emission spectrometry, and NMR. When chimeric protein containing metal radioisotopes is used, the conjugated biological material can be detected by its radioactivity using scintillation counting, $\gamma$-ray counting, and autoradiography. The variety of metal radioisotopes which satisfy specific requirements of the system with respect to the type of emission, half-life, and energy level allows a choise of the appropriate tracer. This technique was used in detecting biotinylated proteins on a blot using the chimeric protein containing radioactive $^{109}$Cd$^{2+}$ as described in Detailed Description of the Invention and Example 5.

A further utility of this invention is a method of simultaneous multi-labeling of many different biological materials with different heavy metal ions, their stable isotopes, and their radioisotopes using the streptavidin-metallothionein chimeric protein of this invention.

Because of very tight binding affinity of the streptavidin-metallothionein chimeric protein, both for biotinylated molecules and heavy metal ions, exchange reactions between biotinylated molecules and between bound heavy metal ions should be prevented. Thus, one can label many different biological materials with different heavy metal ions, their stable isotopes, or their radioisotopes, by conjugating each biological material to the chimeric protein containing one of the heavy metal ions and their isotopes. Such simultaneous multi-labelling of many different biological materials with different metal ions allows the detection and discrimination of each biological material among a number of biological materials with a high sensitivity by the methods described above. In addition, since many metal radioisotopes that can be bound by the chimeric protein emit gamma ($\gamma$)- and X-rays, whose radiations have specific energy levels, one can label many different biological molecules with different metal radioisotopes by using the chimeric protein, and each one of the conjugates can be discriminated from the others by radiochemical characteristics of the attached metal radioisotopes.

Another utility of this invention is a method of detecting biological molecules, such as DNA and proteins, present at very low levels on gels or blots by mass spectrometry.

In this way, biotinylated biological molecules, such as proteins and nucleic acids, are separated by gel electrophoresis and transferred to an appropriate membrane. The streptavidin-metallothionein chimeric protein containing one of the heavy metal ions and their isotopes is conjugated to the biotinylated biological molecules immobilized on the membrane. After unbound chimeric proteins are removed, the conjugates of the biotinylated molecule and the chimeric protein containing one of the metal ions can be detected by surface scanning mass spectrometry, such as sputter-initiated resonance ionization spectroscopy (SIRIS) or laser-atomization resonance ionization spectroscopy (LARIS) coupled with mass spectrometry, with an extremely high sensitivity. Since surface scanning mass spectrometry now allows the detection of heavy metals at the level of around 50 atoms, a biotinylated molecule containing a few biotins, which is able to contain more than 50 atoms of heavy metals by the chimeric protein, can be detected at the single molecule level.

Conjugation of a biotinylated antibody or a biotinylated nucleic acid probe to the chimeric protein containing one of the heavy metals and their isotopes allows to expand the above method to immunoblotting, Southern blotting, and Northern blotting analyses.

Pre-conjugation of a biological molecule to the chimeric protein containing one of the heavy metal ions and their isotopes provides further convenience. The biological molecule pre-conjugated to the chimeric protein containing one of the heavy metal ions is separated by gel electrophoresis. Because of the very high binding affinity of the chimeric protein both for biotinylated molecules and heavy metal ions, no release of the biotinylated molecules and the heavy metal ions from the conjugates occurs during electrophoresis. After the separation, the gel is directly scanned by the surface scanning mass spectrometry described above, and the biological molecule can be detected at the single molecule level through the bound heavy metal ions to the chimeric protein.

The above methods can be further expanded to multi-mass labeling of many different biological molecules with the different heavy metal ions and their isotopes. By conjugating of each biological molecule to the chimeric protein containing one of the different metal isotopes listed in Table 1, many different biological molecules are simultaneously labeled with different heavy metal ions and their isotopes. After separation of the mixture of the labeled biological molecules, each with one of the different heavy metal ions and their isotopes by the chimeric protein, each molecule can be detected and discriminated from the others by surface scanning mass spectrometry described above. As stated above, there are approximately fifty metals and their stable isotopes that can be bound by the chimeric protein. Because of the abundant metal isotopes that can be bound by the chimeric protein, simultaneous multi-mass labeling of different biological molecules with different heavy metal ions and their isotopes using the chimeric protein should substantially increase the number of labels that are attached to different biological molecules, as compared with the current labeling methods such as fluorescence labeling which can discriminate a maximum of only several different labels.

Still another utility of this invention is a method of determining a number of DNA sequences using many different short single-stranded DNA molecules (primers) conjugated to the streptavidin-metallothionein chimeric protein of this invention.

Each synthetic short oligonucleotide containing biotin at its 5'-terminus is conjugated to the chimeric protein containing one of the heavy metals and their isotopes, so that each of the oligonucleotides is labeled with one of the different heavy metals and their isotopes. Each of the oligonucleotides has a complementary sequence to a part of a target DNA whose sequences are to be determined. After annealing the mixture of the labeled oligonucleotides to the target DNA, the dideoxy chain-termination reactions are carried out. Each oligonucleotide serves as the primer in the reaction, and thus each extended single-stranded DNA is labeled with one of the different heavy metal ions and their isotopes conjugated to its primer by the chimeric protein. The reaction mixture is separated by DNA trapping electrophoresis which provides a better resolution of single-stranded DNA molecules when streptavidin is attached to one of the termini of the DNA molecule, and the dried gel is directly scanned by surface scanning mass spectrometry described previously. Since the surface scanning mass spectrometry can detect and discriminate each one of the attached heavy metals and their isotopes from the others, many DNA sequences of the target can be simultaneously determined without any complexity.

These and other medical, whether therapeutic or prophylactic, diagnostic or industrial or other uses are contemplated to be within the scope of this invention.

EXAMPLE 1

Expression of Streptavidin-Metallothionein Chimeric Protein

This example illustrates the expression of streptavidin-metallothionein chimeric protein.

Lysogen BL21 (DE3) (pLysE) transformed with the expression vector pTSAMT-2 was grown at 37° C. with shaking in M9 minimal medium supplemented with 1 mM $MgSO_4$, 0.2% D-glucose, 1.5 µM thiamine (vitamin B1), 0.5% Casamino acids (Difco Laboratories), 2 µg/ml biotin, 150 µg/ml ampicillin, and 25 µg/ml chloramphenicol. When the absorbance at 600 nm of the culture reached values around 0.6, 100 mM of aqueous solution of isopropyl β-D-thiogalactopyranoside was added to a final concentration of 0.5 mM to induce the T7 RNA polymerase gene placed under lacUV5 promoter. After induction, the cells were incubated at 37° C. with shaking.

For pulse-labeling of expressed proteins with [$^{35}$S] cysteine, the culture medium contained 40 µg/ml each natural amino acid except for cysteine, instead of Casamino acids. Pulse-labeling was carried out by incubating 1.0 ml culture with 20 µCi of [$^{35}$S]cysteine (>600 Ci/mmol) at 37° C. for 10 minutes. Total cell protein from 167 µl culture was subjected to SDS-PAGE analysis. The gel was immersed in 20% methanol/10% acetic acid for 20 minutes, and dried in vacuo. The dried gel was exposed to Kodak XAR-5 film.

EXAMPLE 2

Purification of Streptavidin-Metallothionein Chimeric Protein

This example illustrates purification of streptavidin-metallothionein chimeric protein.

All procedures were carried out at 4° C. or on ice. The culture (100 ml), containing lysogen BL21 (DE3) (pLysE) carrying the expression vector pTSAMT-2 incubated for 5 hours after the induction, was centrifuged at 2,900×g for 10 minutes. The cell pellet was suspended in 10 ml of 2 mM EDTA/30 mM Tris-Cl, pH 8.0, containing 0.1% Triton X-100, 10 mM dithiothreitol (DTT), and 0.1 mM phenyl-methylsulfonyl fluoride (PMSF) to lyse the cells. The cell lysate was stored frozen at −70° C.

To the thawed cell lysate (10 ml), PMSF, pepstatin A, and leupeptin were added to final concentrations of 1 mM, 1 μM, and 1 μM, respectively. The addition of the proteinase inhibitors was indispensable to prevent proteolysis of the expressed chimera during purification. The cell lysate was then treated with 10 μg/ml DNase I and 10 μg/ml RNase A in the presence of 12 mM $MgSO_4$ at room temperature (~20° C.) for 30 minutes, followed by centrifugation at 39,000×g for 15 minutes. The precipitate was dissolved in 5 ml of 6 M guanidine hydrochloride, pH 1.5/10 mM DTT, and dialyzed against the same solution to remove bound biotin. To reduce the protein concentration, the dialysate was diluted with the same solution to a total volume of approximately 100 ml, and then dialyzed against 0.2 M ammonium acetate, pH 6.0/0.5 mM $CdCl_2$/0.1 mM EDTA/1 mM PMSF/1 μM pepstatin A/1 μM leupeptin/0.02% $NaN_3$. To achieve slow removal of guanidine hydrochloride, the dialysis bag containing the diluted dialysate was left overnight in the solution (approximately 800 ml) without stirring, followed by several changes of the dialysis solution and dialysis with stirring. The dialysate was again centrifuged at 39,000×g for 15 minutes, and the supernatant was briefly dialyzed against 1.0 M NaCl/50 mM sodium carbonate, pH 10.5/1 mM PMSF/1 μM pepstatin A/1 μM leupeptin. The dialysate was centrifuged at 39,000×g for 15 minutes, and the supernatant was adjusted to pH 10.5 with a 10.0 M NaOH if necessary. The fraction was applied to a 2-iminobiotin agarose column (1.2×1.5 cm; Sigma) previously equilibrated with 1.0 M NaCl/50 mM sodium carbonate, pH 10.5/1 mM PMSF/ 1 μM pepstatin A/1 μM leupeptin. After unbound proteins were removed by washing the column with the same solution, the bound protein was eluted with 6 M urea/50 mM ammonium acetate, pH 4.0/0.5 mM $CdCl_2$/0.1 mM EDTA/1 mM PMSF/1 μM pepstatin A/1 μM leupeptin. The eluted protein fraction was dialyzed against 0.2 M ammonium acetate, pH 7.0/0.5 mM $CdCl_2$/0.1 MM EDTA/1 mM PMSF/ 1 μM pepstatin A/1 μM leupeptin, and then against 0.2 M ammonium acetate, pH 7.0 The dialysate was filtered through a polyvinylidene difluoride filter (pore size 0.22 μm, Millex-GV, Millipore) after centrifugation at 39,000×g for 15 minutes, and the filtrate was stored at 4° C. or at −70° C. for long-term storage.

EXAMPLE 3

Determination of Biotin and Metal-binding Activity

This example illustrates methods to determine biotin and metal-binding ability of streptavidin-metallothionein chimeric protein.

Biotin-binding was determined by gel filtration method described in *Methods Enzymol.*, 18A:424 (1970), using a PD-10 column and D-[carbonyl-$^{14}$C]biotin (53 mCi/mmol).

Quantitative X-ray fluorescence analysis was employed to determine the metal-binding ability. The purified streptavidin-metallothionein chimeric protein (2.3 μg, 120 pmol subunits) was dialyzed at 4° C. against 0.2 M ammonium solution. The dialysate was lyophilized, and dissolved in 18 μl of formic acid (95–97%, Aldrich). The dissolved sample (4 μl) was spotted on a polypropylene membrane obtained from Chemplex Industries, Inc., East Chester, N.Y., and air-dried. The dried sample was subjected to quantitative X-ray fluorescence analysis according to *Analytical Methods Applied to Air Pollution Measurements*, eds. Stevens, R. K., Herget W. F., (Ann Arbor Science, Ann Arbor, Mich. (1974)), to determine the amount of metals in the sample spot. The dialysis solution was used as the control. Standard $CdCl_2$ solution was used for calibration.

EXAMPLE 4

Labeling of Streptavidin-metallothionein Chimeric Protein with Radioactive $Cd^{2+}$ This example illustrates labeling of streptavidin-metallothionein chimeric protein with radioactive cadmium.

The purified streptavidin-metallothionein chimeric protein (68 μg, 3.5 nmol subunits) was dialyzed at 4° C. against 10 mM DTT and then against 10 mM acetic acid, in which Chelex 100 (Bio Rad) was present. To the dialysate, 10 μCi of $^{109}CdCl_2$ (44 Ci/mmol, 0.23 nmol) in 0.1 M HCl and 25 nmol of $ZnCl_2$ in 0.1 M HCl were added. The addition of $Zn^{2+}$ was to saturate the metal-binding sites of the chimera, and was indispensable to avoid aggregation of the chimera due to intermolecular disulfide formation by free sulfhydryl groups. The mixture was then dialyzed at 4° C. against 0.2 M ammonium acetate , pH 7.0, which had been treated with Chelex 100. The dialysed protein was used as the sample. By this procedure, approximately 0.8% of the metal-binding sites contained $^{109}Cd^{2+}$, determined by the liquid scintillation counting and the biotin-binding assay to estimate the protein concentration.

Using essentially the same procedure, streptavidin-metallothionein chimeric protein are labeled with other metal listed in Table 1, as well as their radioisotopes.

EXAMPLE 5

Targeting Streptavidin-metallothionein Chimeric Protein Containing $^{109}Cd^{2+}$ to Biotinylated Macromolecules This example illustrates targeting of streptavidin-metallothionein chimeric proteins containing radioactive $^{109}Cd^{2+}$.

All the procedures were carried out at room temperature, unless otherwise stated. Various amounts (0–5 μg) of biotinylated peroxidase in TBS (150 mM NaCl/20 mM Tris-Cl, pH 7.5/0.02% $NaN_3$) were spotted on a nitrocellulose membrane (0.8×9 cm, pore size 0.45 μm, Schleicher & Schuell). The membrane was incubated with TBS for 10 minutes, and then with 3% gelatin dissolved in TBS for 60 minutes to block free biding sites on the membrane. The membrane was washed with TBS containing 0.02% Tween 20, and incubated for 60 minutes in 1.5 ml of TBS containing 0.02% Tween 10, in which approximately 5 μg of the streptavidin-metallothionein chimera containing $^{109}Cd^{2+}$ prepared as above were incubated. The membrane was then extensively washed with TBS containing 0.02% Tween 20 to remove unbound chimera, and air-dried. The dried membrane was exposed to Kodak XAR-5 film at −70° C. with intensifying screens (Lightning Plus, Du Pont).

EXAMPLE 6

Application of Streptavidin-Metallothionein Fusion Protein for Imaging of Tumors for Radiotherapeutics This example illustrates the utility of the streptavidin-metallothionein chimeric protein for tumor imaging and for radiotherapeutics.

Agents for cancer radiotherapy and for diagnostic uses have been prepared by covalently attaching any of a variety of chelating agents to antibodies, for example, according to *Bioconjugate Chemistry*, 1:222, 345 and 357 (1990), and then adding a metal ion, usually a radionuclide. Monoclonal antibodies show optimal tumor localization only after a few days. Consequently, the choice of radionuclide with the appropriate half-life is essential.

Depending on the ability of the antibody to conjugate with cells in particular tissues, the metal labeled chimeric protein in amount which is sufficient to achieve the cell labeling for diagnostic or for therapeutic purposes is administered to the patient.

For diagnostic purposes, the radiolabeled metal having a short half-life is chosen. For therapeutic purposes where the radioactivity is used for extended localized radiation of organ tumor, the radiolabeled metal having longer time half-life is used.

Copper-67 ($^{67}$Cu) was found to be one of the most promising radiometals for both radioimmunotherapy and imaging because of its 61.5 hour physical half-life, abundant beta particles, and gamma emissions. Paramagnetic complexes, such as those of Mn, Fe, Au, and other various metals have been used as contrast agents for magnetic resonance imaging. The primary requirement is that these complexes have a high kinetic inertness to avoid transfer of the metal ion to competing serum proteins such as transferrin and albumin.

A method to construct conjugates of a monoclonal antibody against B cell lymphoma and radioactive $^{67}$Cu$^+$ is described.

The purified streptavidin-metallothionein chimeric protein (50 μg, 2.6 nmol subunits), which was reconstituted in the presence Cd$^{2+}$ during purification, is dialyzed against 100 mM DTT, and then against 10 mM acetic acid, in which Chelex 100 (Bio Rad) is present to remove any free metal ions in the solutions. Into the dialysate containing the chimeric protein without bound heavy metal ions, 40 nmol $^{67}$Cu$^+$ dissolved in 0.1 M HCl is added and mixed. Because natural metallothionein binds 12 Cu$^+$, the chimeric protein binds total of approximately 31 nmol Cu$^+$. This mixture is extensively dialyzed against PBS (phosphate-buffered saline; 138 mM NaCl, 2.7 mM KCl, 8.1 mM Na$_2$HPO$_4$, 1.1 mM KH$_2$PO$_4$). The metallothionein moiety of the chimeric protein binds the metal ions, and unbound metals are removed. The dialysate containing the protein-$^{67}$Cu$^+$ complexes is mixed with Lym-1, an anti-B cell lymphoma monoclonal antibody (0.39 mg, 2.6 nmol), which has been biotinylated by a standard protocol using biotinyl-N-hydroxysuccinimide. The streptavidin moiety of the chimeric protein binds to the biotin molecule of the antibody, and the biotin-binding sites of the chimeric protein are saturated with the antibody. The resulting chimeric protein-Lym-1 conjugates containing $^{67}$Cu$^+$ are injected into a body to target 67Cu$^+$ to B lymphoma cells. Because the antibody binds to the surface of B lymphoma cells, such cells are irradiated by the radiation of $^{67}$Cu$^+$ conjugated to the antibody and thus selectively killed.

EXAMPLE 7

Labeling of Biological Materials with Heavy Metal Ions or Their Isotopes

This example illustrates the labeling of biological materials with heavy metal ions and their isotopes.

Proteins, nucleic acids, carbohydrates, lipids, cells, tissues, and other biological materials are biotinylated according to the methods summarized in *Methods of Enzymol.*, 814:5–45 (1990). Biotinylated biological material is conjugated to the streptavidin-metallothionein chimeric protein by simply mixing two components at an appropriate ratio. The metallothionein moiety of the chimeric protein is able to bind a variety of heavy metal ions, their stable isotopes, and their radioisotopes. Conjugation of biotinylated biological material to the chimeric protein containing one of such metal ions is used to label the biological material. Detecting and tracking of such biological materials is made by various sensitive methods of choice for detection of heavy metals. X-ray fluorometry, polarography, atomic absorption spectrometry, mass spectrometry, anodic stripping voltammetry, inductively coupled plasma emission spectrometry, and NMR are suitable and very sensitive detection techniques. When the chimeric protein containing metal radioisotopes is used, the conjugated biological material can be detected by its radioactivity using scintillation counting, γ-ray counting, and autoradiography. Variety of metal radioisotopes that bound by the chimeric protein, provides choice of such metal radioisotopes as the tracer. The metal tracer can thus be choosen which satisfies specific requirements of the system with respect to the type of emission, half-life, and energy level.

Typical examples are described in Examples 4 and 5, in which the chimeric protein containing radioactive $^{109}$Cd$^{2+}$ was used to label biotinylated peroxidase immobilized on a nitrocellulose membrane with $^{109}$Cd+ and thus the biotinylated peroxidase was detected by radioactivity.

EXAMPLE 8

Simultaneous Multi-labeling of Many Different Biological Materials with Different Heavy Metal Ions, Their Stable Isotopes, and their Radioisotopes This example, which is an extended application of Example 7, describes a method of simultaneous multi-labeling of many different biological materials with different heavy metal ions, their isotopes, and their radioisotopes using the streptavidin-metallothionein chimeric protein of this invention.

To label many different biological materials with different heavy metal ions, their stable isotopes, or their radioisotopes, each biological material is conjugated to the chimeric protein containing one of the heavy metal ions and their isotopes. Simultaneous multi-labeling of many different biological materials with different metal ions allows the detection and discrimination of each biological material among a number of biological materials with a high sensitivity by the methods described in Example 7. Metal radioisotopes are chosen that can be bound by the chimeric protein and that emit gamma (γ)- and X-rays. These radioisotopes have specific energy levels which can be used to label many different biological molecules with different metal radioisotopes by using the chimeric protein. Each one of the conjugates so labeled can be discriminated from the others by radiochemical characteristics of the attached metal radioisotopes.

This example describes a method to determine the numbers of several cell surface receptors (transferrin receptor, insulin receptor, insulin-like growth factor-I receptor, insulin-like growth factor-II receptor) on a cultured mouse cell, using monoclonal antibodies against these receptors and the chimeric protein.

Monoclonal anti-transferrin receptor antibody (50 μg, 0.33 nmol) is biotinylated by a standard protocol using biotinyl-N-hydroxysuccinimide, and conjugated to the chimeric protein (26 μg, 1.32 nmol subunits) containing Cd$^{2+}$. The resulting conjugate contains one antibody molecule per chimeric protein consisting of four subunits with 28 Cd$^{2+}$. By the same procedure, monoclonal anti-insulin receptor, anti-insulin-like growth factor-I receptor, and anti-insulin-like growth factor-II receptor are biotinylated and labeled with Ni$^{2+}$, Zn$^{2+}$, and Co$^{2+}$, respectively. Mouse fibroblast cell line NTH-3T3 is maintained in monolayer culture in Dulbecco's modified Eagle's medium supplemented with 10% fetal calf serum. The actively growing cells are collected and washed at 4° C. with PBS several times. To the cell suspension in PBS, the mixture of the antibodies labeled with the heavy metal ions is added at 4° C. for 20 minutes, and allowed to bind to the receptor molecules on the cell surface. The cells are washed at 4° C. with PBS several times to remove unbound antibody molecules. The resulting cell pellet is directly subjected to quantitative X-ray fluorescence analysis. Because X-ray fluorescence analysis can detect and discriminate these heavy metals simultaneously and quantitate them by calibration with standard solutions, the number of each bound heavy metal ion can be determined. For example, the number of bound $Cd^{2+}$ is proportional to the number of bound anti-transferrin receptor antibodies and thus to the number of transferrin receptors on the cell surface. Accordingly, the number of transferrin receptors, insulin receptors, insulin-like growth factor-I receptors, and insulin-like growth factor-II receptors on a NIH-3T3 cell can be simultaneously determined.

EXAMPLE 9

Detection of Biological Molecules Present at Very Low Levels on Gels or Blots by Mass Spectrometry This example describes a method of detecting biological molecules, such as DNA and proteins, present at very low levels on gels or blots by mass spectrometry.

Biotinylated biological molecules, according to Example 7, are separated by gel electrophoresis and transferred to an appropriate membrane. The streptavidin-metallothionein chimeric protein containing one of the heavy metal ions and their isotopes is conjugated to the biotinylated biological molecules immobilized on the membrane. After unbound chimeric proteins are removed, the conjugates of the biotinylated molecule and the chimeric protein containing one of the metal ions is detected by surface scanning mass spectrometry, such as sputter-initiated resonance ionization spectroscopy (SIRIS) or laser-atomization resonance ionization spectroscopy (LARIS) coupled with mass spectrometry, with an extremely high sensitivity. Surface scanning mass spectrometry allows the detection of heavy metals at the level of around 50 atoms. Thus, a biotinylated molecule containing a few biotins, which is able to contain more than 50 atoms of heavy metals by the chimeric protein, is detected at the single molecule level.

Conjugation of a biotinylated antibody or a biotinylated nucleic acid probe to the chimeric protein containing one of the heavy metals and their isotopes is used for immunoblotting, Southern blotting, and Northern blotting analyses.

Pre-conjugation of a biological molecule to the chimeric protein containing one of heavy metal ions and their isotopes provides further uses. The biological molecule pre-conjugated to the chimeric protein is separated by gel electrophoresis. Because of the very high binding affinity of the chimeric protein both for biotinylated molecules and heavy metal ions, no release of the biotinylated molecules and the heavy metal ions from the conjugates occurs during electrophoresis. After the separation, the gel is directly scanned by the surface scanning mass spectrometry described above, and the biological molecule is detected at the single molecule level through the bound heavy metal ions to the chimeric protein.

The above methods are easily expanded to multi-mass labeling of many different biological molecules with different metal ions and their isotopes. By conjugating each biological molecule to the chimeric protein containing one of the different metal ions and their isotopes, many different biological molecules are simultaneously labeled with different heavy metal ions and their isotopes. After separation of the mixture of the labeled biological molecules, each with one of the different heavy metal ions and their isotopes by the chimeric protein, each molecule can be detected and discriminated from the others by surface scanning mass spectrometry described above. Since many stable metal isotopes are available as described above and listed in Table 1, the simultaneous multi-mass labeling method substantially increases the number of labels that are attached to different biological molecules and thus allow simultaneous assays for large numbers of biological targets.

A method to determine the number of epidermal growth factor receptors in specific human cells, which are available only in very small amounts, is described below.

Lysate of human cells of interest is prepared by standard methods, separated by acrylamide gel electrophoresis, and blotted on a nitrocellulose membrane. Mouse monoclonal anti-epidermal growth factor receptor antibody (50 μg, 0.33 nmol) is biotinylated by a standard protocol using biotinyl-N-hydroxysuccinimide, and conjugated to the streptavidin-metallothionein chimeric protein containing $Zn^{2+}$ (26 μg, 1.3 nmol). Thus each antibody molecule is conjugated to one chimeric protein molecule containing 28 $Zn^{2+}$. The membrane containing human cell lysates is incubated in 3% gelatin dissolved in TBS (Tris-buffered saline, 150 mM NaCl, 20 mM Tris-Cl, pH 7.5, 0.02% $NaN_3$) to block the free binding sites of the membrane, and then incubated with the antibody-chimeric protein-$Zn^{2+}$ conjugates in TBS containing 1% gelatin and 0.02% Tween 20. The membrane is washed with TBS containing 0.02% Tween 20 to remove unbound antibody-chimeric protein conjugates, and air-dried. The dried membrane is subjected to surface scanning mass spectrometry to quantitate the amount of Zn in each lane. The number of epidermal growth factor receptors in each lane is proportional to the amount of Zn, and thus can be determined after the calibration.

By this method, very small numbers of epidermal growth factor receptor can be accurately determined, because of the extremely high sensitivity and accuracy of surface scanning mass spectrometry.

EXAMPLE 10

Simultaneous Multi-Mass Labeling of Short DNA Molecules Allowing Determination of A Number of DNA Sequences This example is a further application of Example 9, and describes a method of determining a number of DNA sequences using many different short single-stranded DNA molecules (primers) conjugated to the streptavidin-metallothionein chimeric protein of this invention.

Each synthetic short oligonucleotide containing biotin at its 5'-terminus is conjugated to the chimeric protein containing one of the heavy metals and their isotopes, so that each of the oligonucleotides is labeled with one of the different heavy metals and their isotopes. Each of the oligonucleotides has a complementary sequence to a part of a target DNA whose sequences are to be determined. After annealing the mixture of the labeled oligonucleotides to the target DNA, the dideoxy chain-termination reactions according to *Proc. Nat'l. Acad. Sci.*, 74:5463 (1977) are carried out. Each oligonucleotide serves as a the primer in the reaction, and thus each extended single-stranded DNA is labeled with one of the different heavy metal ions and their isotopes conjugated to its primer by the chimeric protein. The reaction mixture is separated by DNA trapping electrophoresis according to *Nature,* 343:190 (1990) which provides a better resolution of single-stranded DNA molecules when streptavidin is attached to one of the termini of the DNA molecule, and the dried gel is directly scanned by surface scanning spectrometry described in Example 9. Since surface scanning mass spectrometry can detect and discriminate each one of the attached heavy metals and their isotopes from the others, many DNA sequences of the target can be simultaneously determined without any complexity.

A method to efficiently determine the DNA sequences of a cosmid clone containing a human DNA (35 kb) of interest is described below.

Forty different plasmid vectors are constructed from a parental vector. Each vector contains a unique 20-mer DNA sequence (primer binding site), which is different from those of the rest of the vectors, adjacent to a common cloning site (Sau3A I; recognition sequence, GATC). Forty different biotinylated 20-mer oligonucleotides (primers), each of which has a complementary sequence to the primer binding site of one of the vectors, are synthesized by standard methods using an automated DNA synthesizer. Each primer contains a biotin molecule at its 5'-terminus, and is conjugated to streptavidin-metallothionein chimeric protein containing one of the available heavy metal stable isotopes (Table 1). These primers are mixed together (primer mixture). The insert region of the cosmid clone is partially digested with Sau3A I, and the resulting fragments are randomly ligated into a set of the forty vectors independently, which have been digested with Sau3A I and treated with phosphatase. *E. coli* cells are transformed with the ligation mixtures, and forty sets of transformants, each set derived from one of the forty different vectors, are obtained. A single colony from each of the forty sets of transformants is picked up, and combined together, so that the resulting mixture contains forty different clones, each of which is derived from one of the forty different vectors. Nine more mixtures are prepared by repeating the above procedures. Each mixture is subjected to PCR sequencing reactions using the primer-chimeric protein-heavy metal complexes. No dissociation of the complexes occurs during the reaction because of the high binding affinity both for biotinylated DNA and heavy metal ions. Since surface scanning mass spectrometry possesses extremely high sensitivity, only few cycles of reaction are required. The reaction mixture is separated by DNA trapping electrophoresis, and the gel containing ten independent reaction mixtures is dried. The dried gel is scanned by surface scanning mass spectrometry, and the DNA sequences of each clone can be read by tracking one of the heavy metal isotopes used. If each sequencing reaction with one of the primers could determine 300 bp of DNA sequence, one reaction with a mixture of forty clones can generate 12 kb of sequence. Thus one gel containing ten independent reaction mixtures, each containing forty independent clones, should be able to determine 120 kb of sequence, which gives more than 3-fold redundancy over the original sequence in the cosmid clone. Thus enough overlaps can be found in the determined DNA sequence to determine the orientation and relationships among the subclones. By this method, the sequences of the cosmid clone containing 35 kb human DNA can be determined with 10 independent sequencing reactions.

What is claimed is:

1. A method of making a recombinant bifunctional streptavidin-metallothionein chimeric protein, said method comprising steps:

(a) introducing into a host cell a nucleic acid encoding a bifunctional fusion protein comprising a streptavidin moiety and a metallothionein moiety, wherein said streptavidin moiety consists of residues 16 to 133 (SEQ ID NO:7) of mature streptavidin;

(b) incubating said cell under conditions sufficient to express said fusion protein;

(c) isolating said fusion protein.

2. A method according to claim 1, wherein said isolating step comprises a renaturation step in the presence of a heavy metal ion which binds said metallothionein moiety.

3. A method according to claim 1, wherein said fusion protein additionally comprises a peptide between said streptavidin moiety and said metallothionein moiety.

4. A method according to claim 1, wherein said conditions comprise a medium sufficiently minimal to substantially reduce proteolysis of the expressed chimeric protein.

5. A method according to claim 1, wherein said isolating step is performed at least in part in the presence of one or more proteinase inhibitors sufficient to reduce proteolysis.

6. A method according to claim 1, wherein said isolating step is performed at least in part in the presence of dithiothreitol.

7. A method according to claim 1, wherein said isolating step comprises 2-iminobiotin affinity chromatography performed at least in part at a pH of 10.5.

8. A method of making a bifunctional recombinant streptavidin-metallothionein chimeric protein, said method comprising steps:

(a) introducing into a host cell a nucleic acid encoding a fusion protein comprising a streptavidin moiety and a metallothionein moiety, wherein said streptavidin moiety consists of residues 16 to 133 (SEQ ID NO: 7) of mature streptavidin, and said fusion protein additionally comprises a peptide between said streptavidin moiety and said metallothionein moiety;

(b) incubating said cell under conditions sufficient to express said fusion protein, wherein said conditions comprise a medium sufficiently minimal to substantially reduce proteolysis of the expressed chimeric protein;

(c) isolating said fusion protein, said isolating step performed at least in part in the presence of one or more proteinase inhibitors sufficient to reduce proteolysis and at least in part in the presence of dithiothreitol, wherein said isolating step comprises 2-iminobiotin affinity chromatography performed at a pH of 10.5.

9. A method according to claim 8, wherein said isolating step a renaturation step in the presence of a heavy metal ion which binds said metallothionein moiety.

10. A bifunctional recombinant streptavidin-metallothionein chimeric protein, said protein made by a method comprising steps:

(a) introducing into a host cell a nucleic acid encoding a bifunctional fusion protein comprising a streptavidin moiety and a metallothionein moiety, wherein said streptavidin moiety consists of residues 16 to 133 (SEQ ID NO: 7) of mature streptavidin;

(b) incubating said cell under conditions sufficient to express said fusion protein;

(c) isolating said fusion protein.

11. A recombinant streptavidin-metallothionein chimeric protein according to claim 10, wherein said fusion protein additionally comprises a peptide between said streptavidin moiety and said metallothionein moiety.

12. A recombinant streptavidin-metallothionein chimeric protein according to claim 10, wherein said conditions comprise a medium sufficiently minimal to substantially reduce proteolysis of the expressed chimeric protein.

13. A recombinant streptavidin-metallothionein chimeric protein according to claim 10, wherein said isolating step is performed at least in part in the presence of one or more proteinase inhibitors sufficient to reduce proteolysis.

14. A recombinant streptavidin-metallothionein chimeric protein according to claim 10, wherein said isolating step performed at least in part in the presence of dithiothreitol.

15. A recombinant streptavidin-metallothionein chimeric protein according to claim 10, wherein said isolating step comprises a renaturation step in the presence of a heavy metal ion which binds said metallothionein moiety.

16. A bifunctional recombinant streptavidin-metallothionein chimeric protein, said protein made by a method comprising steps:

(a) introducing into a host cell a nucleic acid encoding a fusion protein comprising a streptavidin moiety and a metallothionein moiety, wherein said streptavidin moiety consists of residues 16 to 133 (SEQ ID NO:7) of mature streptavidin, and said fusion protein additionally comprises a peptide between said streptavidin moiety and said metallothionein moiety;

(b) incubating sad cell under conditions sufficient to express said fusion protein;

(c) isolating said fusion protein, said isolating step performed at least in part in the presence of one or more proteinase inhibitors sufficient to reduce proteolysis and at least in part in the presence of dithiothreitol.

17. A recombinant streptavidin-metallothionein chimeric protein according to claim 16, wherein said isolating step comprises 2-iminobiotin affinity chromatography performed at least in part at a pH of 10.5.

18. A bifunctional recombinant streptavidin-metallothionein chimeric protein, wherein said protein comprises a streptavidin moiety and a metallothionein moiety, and said streptavidin moiety consists of residues 16 to 133 (SEQ ID NO:7) of mature streptavidin.

19. A bifunctional recombinant streptavidin-metallothionein chimeric protein comprising a streptavidin moiety and a metallothionein moiety, wherein said streptavidin moiety consists of residues 16 to 133 (SEQ ID NO:7) of mature streptavidin, and said fusion protein additionally comprises a peptide between said streptavidin moiety and said metallothionein moiety.

20. An expression vector comprising a truncated streptavidin gene encoding a streptavidin moiety wherein said streptavidin moiety consists of residues 16 to 133 of mature streptavidin (SEQ ID NO:7).

21. An expression vector according to claim 20, wherein said truncated streptavidin gene is under the transcriptional control of a T7 promoter.

22. An expression vector according to claim 20, wherein said truncated streptavidin gene is joined to a polylinker comprising a cloning site.

23. An expression vector according to claim 20, comprising a gene fusion of said truncated streptavidin gene and a target protein gene.

24. An expression vector according to claim 20, comprising a gene fusion of said truncated streptavidin gene and a target protein gene, wherein said target protein gene encodes metallothionein.

25. A bifunctional recombinant streptavidin chimeric protein, wherein said protein comprises a streptavidin moiety consisting of residues 16 to 133 (SEQ ID NO:7) of mature streptavidin.

26. A chimeric protein comprising a functional streptavidin moiety consisting of residues 16 to 133 (SEQ ID NO:7) of mature streptavidin.

27. A functional streptavidin consisting of residues 16 to 133 (SEQ ID NO:7) of mature streptavidin.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 66 base pairs
      (B) TYPE: nucleic acid
      (C) STRANDEDNESS: double
      (D) TOPOLOGY: linear    (ii) MOLECULE TYPE: cDNA    (ix) FEATURE:
      (A) NAME/KEY: CDS
      (B) LOCATION: 1..61

(xi) SEQUENCE DESCRIPTION: SEQ ID NO:1:

```
AAG GTG AAT TCG AGC TCG GTA CCC GGG GAT CCT CTA GAG TCG ACC TGC      48
Lys Val Asn Ser Ser Val Pro Gly Asp Pro Leu Glu Ser Thr Cys
  1               5                  10                  15

AGG CAT GCA AGC TTC GAT                                              66
Arg His Ala Ser Phe Asp
             20
```

(2) INFORMATION FOR SEQ ID NO:2:

(i) SEQUENCE CHARACTERISTICS:
      (A) LENGTH: 22 amino acids
      (B) TYPE: amino acid
      (D) TOPOLOGY: linear (ii) MOLECULE TYPE: protein (xi) SEQUENCE DESCRIPTION: SEQ ID NO:2:

```
Lys Val Asn Ser Ser Val Pro Gly Asp Pro Leu Glu Ser Thr Cys
 1               5                  10                  15
Arg His Ala Ser Phe Asp
             20
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: double
        (D) TOPOLOGY: linear     (ii) MOLECULE TYPE: cDNA     (ix) FEATURE:
        (A) NAME/KEY: CDS
        (B) LOCATION: 1..30

(xi) SEQUENCE DESCRIPTION: SEQ ID NO:3:

```
AAT TCG AGC TCG GTA CCC GGG GAT CTC GGA                         30
Asn Ser Ser Ser Val Pro Gly Asp Leu Gly
                 25                  30
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear     (ii) MOLECULE TYPE: protein     (xi) SEQUENCE DESCRIPTION: SEQ ID NO:4:

```
Asn Ser Ser Ser Val Pro Gly Asp Leu Gly
 1               5                  10
```

(2) INFORMATION FOR SEQ ID NO:5:

(i) SEQUENCE CHARACTERISTICS:
        (A) LENGTH: 62 amino acids
        (B) TYPE: amino acid
        (C) STRANDEDNESS: Not Relevant
        (D) TOPOLOGY: Not Relevant     (ii) MOLECULE TYPE: peptide     (xi) SEQUENCE DESCRIPTION: SEQ ID NO:5:

```
Met Asp Pro Asn Cys Ser Cys Ala Thr Gly Gly Ser Cys Thr Cys Ala
 1               5                  10                  15
Gly Ser Cys Lys Cys Lys Glu Cys Lys Cys Thr Ser Cys Lys Lys Ser
                20                  25                  30
Cys Cys Ser Cys Cys Pro Val Gly Cys Ala Lys Cys Ala Gln Gly Cys
            35                  40                  45
Val Cys Lys Ala Gly Ala Ser Asp Lys Cys Ser Cys Cys Ala
    50                  55                  60
```

(2) INFORMATION FOR SEQ ID NO:6:

(i) SEQUENCE CHARACTERISTICS:
        (A) LENGTH: 354 base pairs
        (B) TYPE: nucleic acid
        (C) STRANDEDNESS: double

```
        (D) TOPOLOGY: linear (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:6:

GGC ATC ACC GGC ACC TGG TAC AAC CAG CTC GGC TCG ACC TTC ATC GTG       48
Gly Ile Thr Gly Thr Trp Tyr Asn Gln Leu Gly Ser Thr Phe Ile Val
                15                  20                  25

ACC GCG GGC GCC GAC GGC GCC CTG ACC GGA ACC TAC GAG TCG GCC GTC       96
Thr Ala Gly Ala Asp Gly Ala Leu Thr Gly Thr Tyr Glu Ser Ala Val
            30                  35                  40

GGC AAC GCC GAG AGC CGC TAC GTC CTG ACC GGT CGT TAC GAC AGC GCC      144
Gly Asn Ala Glu Ser Arg Tyr Val Leu Thr Gly Arg Tyr Asp Ser Ala
        45                  50                  55

CCG GCC ACC GAC GGC AGC GGC ACC GCC CTC GGT TGG ACG GTG GCC TGG      192
Pro Ala Thr Asp Gly Ser Gly Thr Ala Leu Gly Trp Thr Val Ala Trp
    60                  65                  70

AAG AAT AAC TAC CGC AAC GCC CAC TCC GCG ACC ACG TGG AGC GGC CAG      240
Lys Asn Asn Tyr Arg Asn Ala His Ser Ala Thr Thr Trp Ser Gly Gln
75                  80                  85                  90

TAC GTC GGC GGC GCC GAG GCG AGG ATC AAC ACC CAG TGG CTG CTG ACC      288
Tyr Val Gly Gly Ala Glu Ala Arg Ile Asn Thr Gln Trp Leu Leu Thr
                95                 100                 105

TCC GGC ACC ACC GAG GCC AAC GCC TGG AAG TCC ACG CTG GTC GGC CAC      336
Ser Gly Thr Thr Glu Ala Asn Ala Trp Lys Ser Thr Leu Val Gly His
            110                 115                 120

GAC ACC TTC ACC AAG GTG                                              354
Asp Thr Phe Thr Lys Val
        125

(2) INFORMATION FOR SEQ ID NO:7:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:7:

Gly Ile Thr Gly Thr Trp Tyr Asn Gln Leu Gly Ser Thr Phe Ile Val
 1               5                  10                  15

Thr Ala Gly Ala Asp Gly Ala Leu Thr Gly Thr Tyr Glu Ser Ala Val
            20                  25                  30

Gly Asn Ala Glu Ser Arg Tyr Val Leu Thr Gly Arg Tyr Asp Ser Ala
        35                  40                  45

Pro Ala Thr Asp Gly Ser Gly Thr Ala Leu Gly Trp Thr Val Ala Trp
    50                  55                  60

Lys Asn Asn Tyr Arg Asn Ala His Ser Ala Thr Thr Trp Ser Gly Gln
65                  70                  75                  80

Tyr Val Gly Gly Ala Glu Ala Arg Ile Asn Thr Gln Trp Leu Leu Thr
                85                  90                  95

Ser Gly Thr Thr Glu Ala Asn Ala Trp Lys Ser Thr Leu Val Gly His
            100                 105                 110

Asp Thr Phe Thr Lys Val
        115
```